United States Patent
Ishikawa (10) Patent No.: US 7,327,871 B2
(45) Date of Patent: Feb. 5, 2008

(54) DEFECT INSPECTING METHOD, DEFECT INSPECTING APPARATUS AND INSPECTION MACHINE

(75) Inventor: Akio Ishikawa, Hachioji (JP)

(73) Assignee: Tokyo Seimitsu Co., Ltd., Tokyo (JP)

( * ) Notice: Subject to any disclaimer, the term of this patent is extended or adjusted under 35 U.S.C. 154(b) by 721 days.

(21) Appl. No.: 10/875,040

(22) Filed: Jun. 22, 2004

(65) Prior Publication Data

US 2004/0264760 A1    Dec. 30, 2004

(30) Foreign Application Priority Data

Jun. 30, 2003    (JP)    ............... 2003-188153

(51) Int. Cl.
    *G06K 9/00*    (2006.01)
(52) U.S. Cl. ...................... 382/145; 345/582
(58) Field of Classification Search ................ 382/145; 345/582

See application file for complete search history.

(56) References Cited

U.S. PATENT DOCUMENTS 6,356,300 B1 *    3/2002    Shiba ........................ 348/130
6,504,948 B1 *    1/2003    Schemmel et al. ......... 382/149
6,865,288 B1 *    3/2005    Shishido et al. ............ 382/145
2003/0138138 A1 *    7/2003    Vacca et al. ................ 382/145

FOREIGN PATENT DOCUMENTS

JP    2000-323541    11/2000

OTHER PUBLICATIONS

Patent Abstracts of Japan for Publication No. 2000323541, publication date Nov. 24, 2000, in the name of Kuwabara Masayuki et al.

* cited by examiner

*Primary Examiner*—Matthew C. Bella
*Assistant Examiner*—Mike Rahmjoo
(74) *Attorney, Agent, or Firm*—Christie, Parker & Hale, LLP (57) ABSTRACT

According to a defect inspecting method implemented in a semiconductor circuit inspection machine, a difference in a gray-scale level of a pattern edge image is corrected. A procedure of determining a magnitude of correction is modified in efforts to improve the sensitivity in detecting a defective pattern edge image. A defect inspecting system comprises: an image alignment unit that detects a sub-pixel deviation of two images, which are objects of inspection, from each other; and a magnitude-of-correction determination unit that determines a magnitude of correction, by which the difference in a gray-scale level of a pattern edge image between the two images that is detected by the difference detector is corrected, according to the detected sub-pixel deviation.

12 Claims, 12 Drawing Sheets

3 × 3 FILTER $$\begin{pmatrix} a_{-1-1} & a_{-10} & a_{-11} \\ a_{0-1} & a_{00} & a_{01} \\ a_{1-1} & a_{10} & a_{11} \end{pmatrix}$$

Fig.11C $$A*GL(x,y)=\sum_{i=-1}^{1}\sum_{j=-1}^{1} a_{ij} GL(x-j, y-i)$$

X-DIRECTION
DIFFERENTIAL FILTER

Fig.12A $\quad dX = \begin{pmatrix} -1 & 0 & 1 \\ -2 & 0 & 2 \\ -1 & 0 & 1 \end{pmatrix}$

Fig.12B

BEFORE FILTERING
IS PERFORMED

| | | 48 | 49 | | |
|---|---|---|---|---|---|
| 5 | 5 | 5 | 10 | 10 | 10 |
| 5 | 5 | 5 | 10 | 10 | 10 |
| 5 | 5 | 5 | 10 | 10 | 10 |
| 5 | 5 | 5 | 10 | 10 | 10 |
| 5 | 5 | 5 | 10 | 10 | 10 |
| 5 | 5 | 5 | 10 | 10 | 10 |

Fig.12C

AFTER FILTERING
PERFORMED

| | | 48 | 49 | | |
|---|---|---|---|---|---|
| 0 | 0 | 20 | 20 | 0 | 0 |
| 0 | 0 | 20 | 20 | 0 | 0 |
| 0 | 0 | 20 | 20 | 0 | 0 |
| 0 | 0 | 20 | 20 | 0 | 0 |
| 0 | 0 | 20 | 20 | 0 | 0 |
| 0 | 0 | 20 | 20 | 0 | 0 |

DEFECT INSPECTING METHOD, DEFECT INSPECTING APPARATUS AND INSPECTION MACHINE

CROSS REFERENCE TO RELATED APPLICATION

This application is based upon and claims the benefit of priority from the prior Japanese Patent Application No. 2003-188153, filed on Jun. 30, 2003, the entire contents of which are incorporated herein by reference.

BACKGROUND OF THE INVENTION

1. Field of the Invention

The present invention relates to a defect inspecting method and an apparatus that detect a difference between corresponding signals, that compare the detected difference with a threshold, and that, if the difference is larger than the threshold, judge that one of the signals is defective. More particularly, the present invention is concerned with a defect inspecting method and an apparatus that detect a difference in a gray-scale level of one of corresponding portions of two images derived from two objects, that compare the detected difference in a gray-scale level with a threshold, and that if the difference in a gray-scale level is larger than the threshold, judge that one of the objects is defective. Moreover, the present invention is concerned with an inspection machine that detects a defective semiconductor circuit pattern formed on a semiconductor wafer according to said defect inspecting method.

2. Description of the Related Art

The present invention refers to an image processing method and apparatus that compare corresponding portions of two images derived from two objects, which are supposed to be identical to each other, with each other, and that if the difference between the corresponding portions is large, judge that one of the objects is defective. Herein, a description will be made by taking for instance an inspection machine that detects a defective semiconductor circuit pattern formed on a semiconductor wafer in a semiconductor manufacturing process. However, the present invention is not limited to the inspection machine.

Moreover, generally, inspection machines are realized with bright-field inspection machines that illuminate the surface of an object with light falling on the surface vertically and capture an image represented by reflected light. Dark field inspection machines that do not directly capture illumination light are also in use. In the case of the dark field inspection machine, the surface of an object is illuminated with light falling on the surface obliquely or vertically, and a sensor is disposed so that it will not detect regularly reflected light. Spots illuminated with illumination light are successively scanned in order to produce a dark field image of the surface of the object. Some dark field inspection machines do not employ an image sensor. The present invention encompasses this type of dark field inspection machine. The present invention is adaptable to any image processing method and apparatus which compare corresponding portions of two images (image signals) derived from two objects that are supposed to be identical to each other. Herein, if the difference is large, the image processing method and apparatus judge that one of the objects the images is defective.

In a semiconductor manufacturing process, numerous chips (dice) are formed on a semiconductor wafer. Each die is patterned in multiple layers. The completed die is electrically inspected using a prover and a tester, and a defective die is excluded from an assembling step. What counts greatly in the semiconductor manufacturing process is the yield. The result of the electric inspection is fed back to the manufacturing process and reviewed for the management of processing steps.

However, the semiconductor manufacturing process comprises numerous steps. It takes much time until the electric inspection is started after the start of manufacture. Consequently, when the electric inspection reveals that the semiconductor manufacturing process has a drawback, numerous wafers have already been processed. The result of the electric inspection cannot be fully utilized for improvement. Therefore, defective pattern inspection is performed for inspecting every pattern formed at an intermediate step so as to detect a defect. If the defective pattern inspection is performed at a plurality of steps among all steps, a defect occurring after a previous inspection can be detected. The result of inspection can be swiftly fed back for management of the steps processing.

In currently available inspection machines, a semiconductor wafer is illuminated, and an image of a semiconductor circuit pattern is optically captured in order to produce an electric image signal. The electric image signal is converted into a multi-valued digital signal (digital gray-scale level signal). A difference signal (gray-scale level difference signal) is produced. Herein, the difference signal represents a difference from a gray-scale level signal that represents a reference pattern. When the difference is larger than a predetermined threshold, the pattern is judged to be defective (refer to, for example, Japanese Unexamined Patent Publication No. 2000-323541). The reference pattern is generally a pattern formed on an adjoining die or an adjoining identical pattern.

Figure 6:
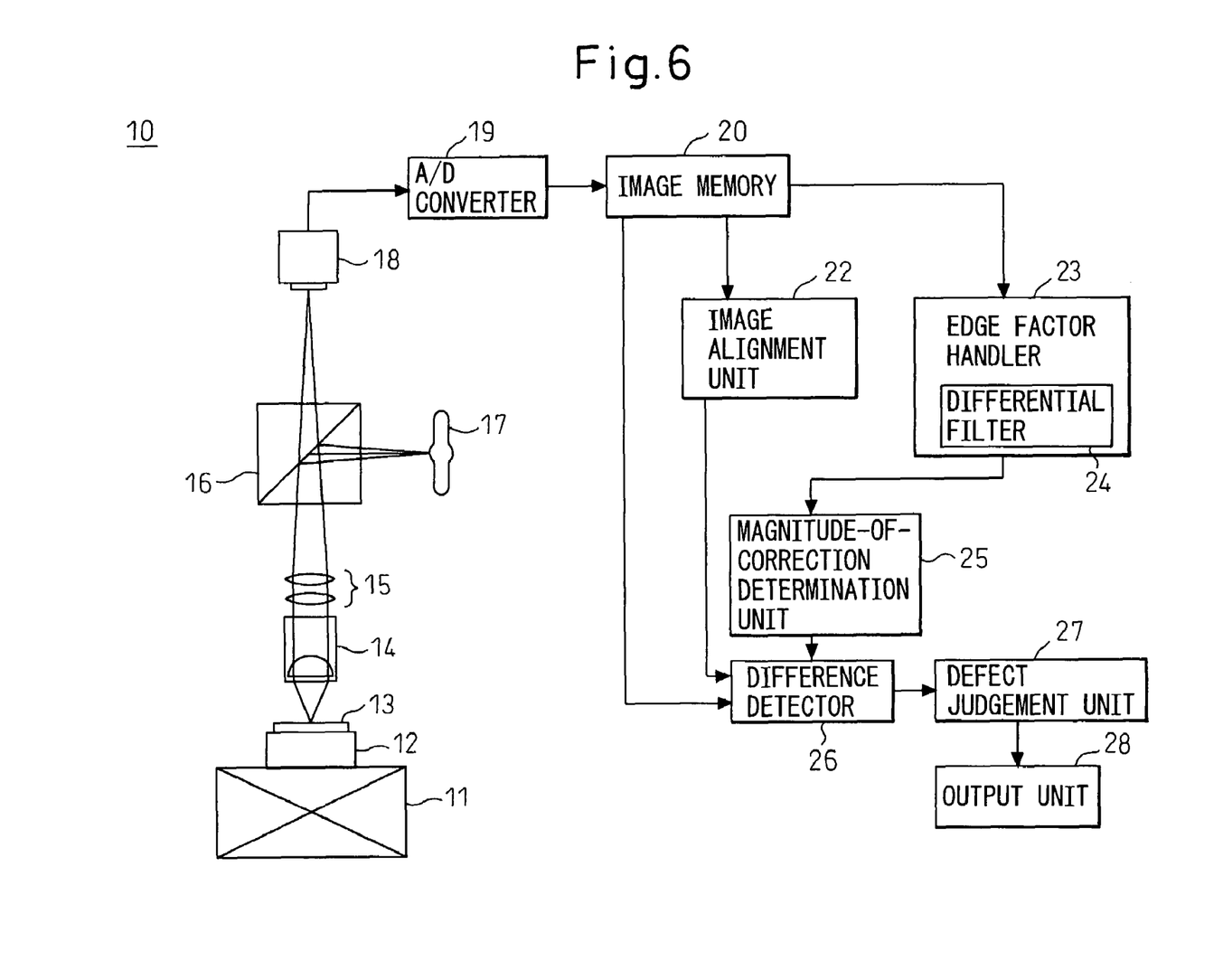
FIG. 6 schematically shows the configuration of a conventional semiconductor device inspection apparatus.

FIG. 6 schematically shows the configuration of a conventional semiconductor device inspection machine. Referring to the drawing, an inspection machine 10 comprises: a high-precision xy stage 11 that is movable in the x and y directions; a wafer chuck 12 fixed to the xy stage 11; an objective lens 14; a tube lens 15; a beam splitter 16; a light source 17; an optical imaging unit 18 such as a TDI camera; an analog-to-digital (A/D) converter 19; an image memory 20; an image alignment unit 22; a difference detector 26; a defect judgement unit 27; and an output unit 28.

Figure 7:
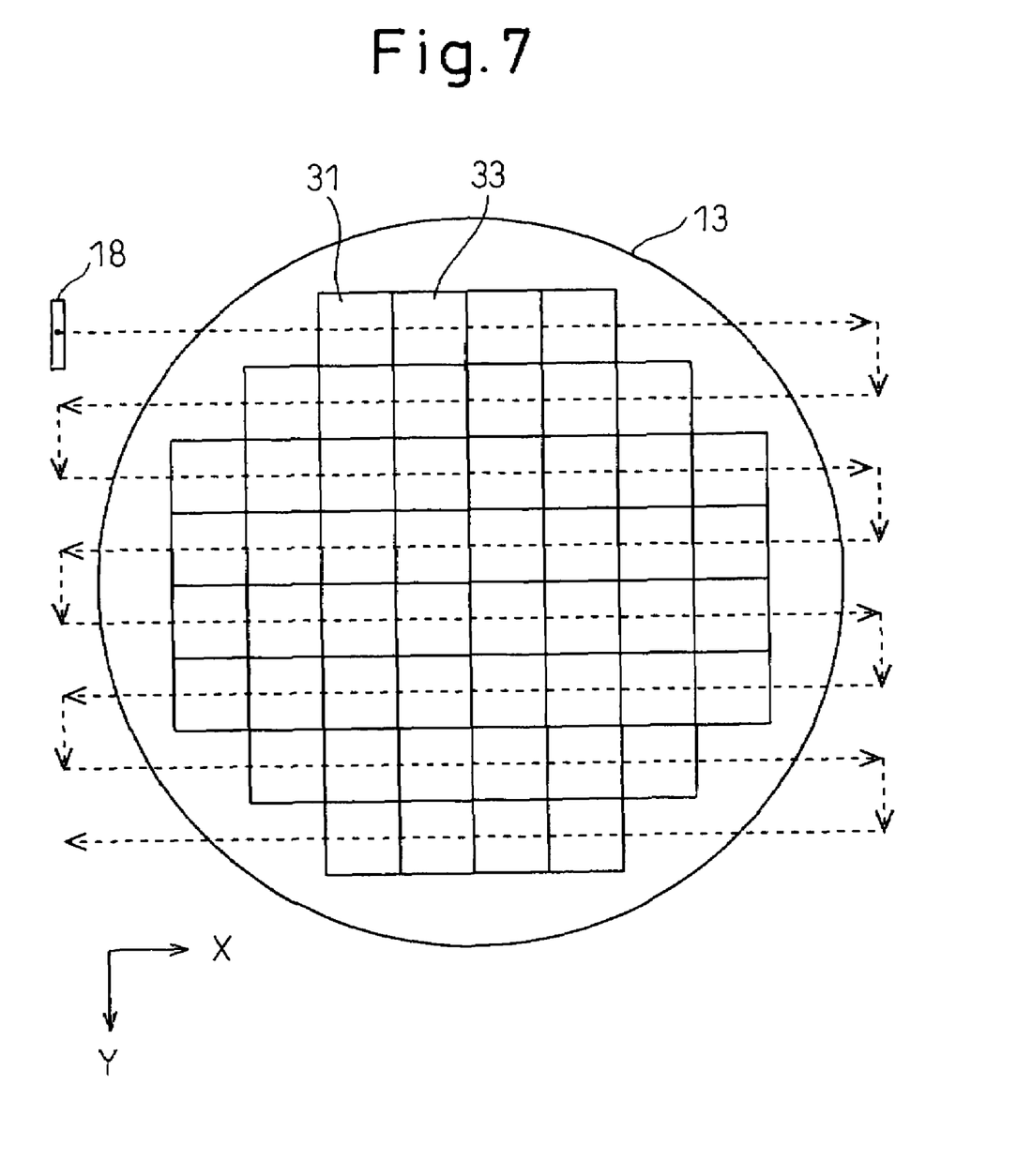
FIG. 7 illustrates a wafer.

When the xy stage 11 moves a wafer 13, the imaging unit 18 scans the wafer 13 in the x and y directions and images the entire surface of the wafer 13. FIG. 7 illustrates the wafer 13. As illustrated, numerous dice 31 and 33 etc. having substantially the same pattern formed thereon are formed orderly on the wafer 13. The imaging unit 18 scans the wafer 13 as indicated with arrows in the drawing so as to image the surface of the wafer. A image signal produced by the imaging unit 18 is analog-to-digital converted and then stored in the image memory 20.

Figure 8A:
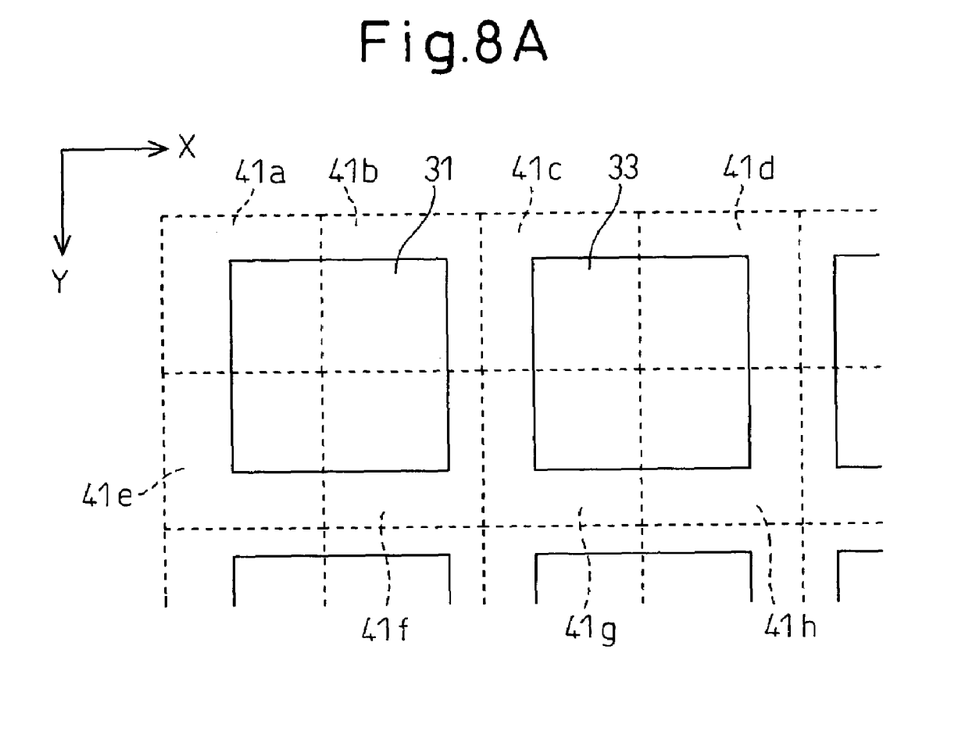
FIG. 8A and FIG. 8B illustrate part of an image representing a wafer 13.

FIG. 8A illustrates part of a produced image representing the surface of the wafer 13 having been analog-to-digital converted. An area surrounded with a dot line in the drawing corresponds to the part of the image. As illustrated, the image is divided into image (41a to 41h) having a certain number of pixels. In units of the image domain, a produced image of an inspected pattern is aligned with a produced image of a reference pattern. The alignment will be described later.

If the imaging unit 18 is a line sensor, the number of pixels in the Y direction within the image domain 41 generally agrees with the number of pixel locations in the imaging unit 18. The number of pixels constituting the image domain 41 is, for example, a product of 2048 pixels by 2048 pixels.

Figure 8B:
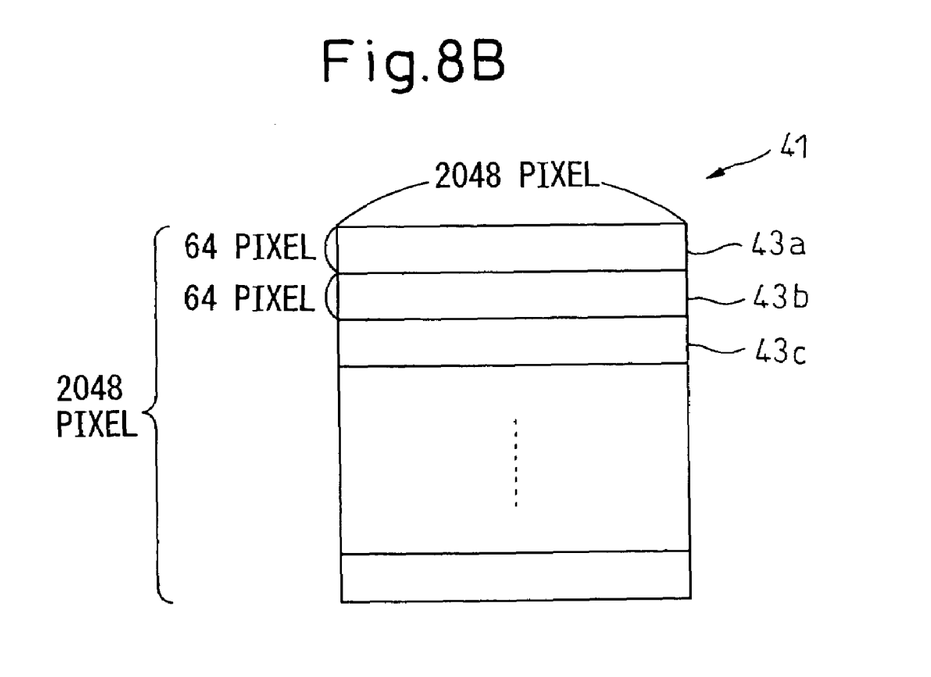

FIG. 8B illustrates an image corresponding to one image domain 42. As illustrated, the image domain is divided into frames (43a, 43b, 43c, ... 43h) having a certain number of pixels. The aforesaid defect inspection is performed in units of one frame. For the defect inspection, a difference-in-gray-scale level signal representing a difference in a gray-scale level between a frame (inspected frame) included in a produced image of an inspected die and a frame (reference frame) included in a produced image of a reference die is produced. The number of pixels constituting one frame is, for example, a product of 2048 pixels by 64 pixels.

Generally, the dimension of each image domain 41 is defined differently from the dimension of each die 31. Therefore, in order to produce the difference-in-gray-scale level signal representing the difference in a gray-scale level between the inspected frame and reference frame, it must be sensed in what image domains 41 the frames belong and at what positions in image domains 41 the frames are located. Thereafter, the frames must be aligned with each other. An alignment procedure will be described below.

First, the image alignment unit 22 aligns an inspected frame and a reference frame with each other by shifting the frames to a degree measured in units of a pixel. This alignment shall be referred to as pixel alignment. In the pixel alignment, first, a database containing semiconductor circuit design CAD data is referenced in order to determine in what image domains 41 the inspected frame and reference frame belong. For example, a die 31 shall be a reference die, and a die 33 shall be an inspected die. A domain 41a containing a left upper domain of an image representing the reference die 31, and a domain 41c containing a left upper domain of an image representing the inspected die 33 are determined (see FIG. 8A).

Figure 9A:
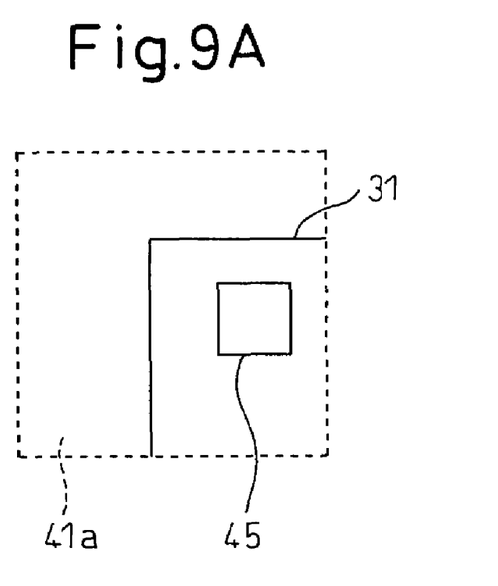
FIG. 9A and FIG. 9B are explanatory diagrams concerning pixel alignment.
Figure 9B:
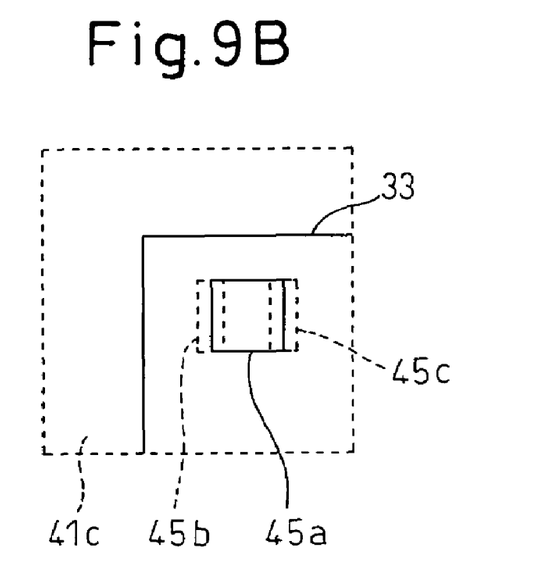

Thereafter, an alignment reference image 45 corresponding to a predetermined position in the image of the reference die 31 is sampled from the domain 41a. An image 45a having the same size as the alignment reference image 45 and corresponding to a predetermined position in the image of the inspected die 33 is sampled from the domain 41c. Moreover, several images are sampled from the domain 41c by shifting the image 45a to a degree measured in units of a pixel. For example, an image 45b is sampled by shifting the image 45a by one pixel in the x direction, and an image 45c is sampled by shifting the image 45a by one pixel in the −x direction. FIG. 9A illustrates the alignment reference image 45 that is a portion of the image produced to represent the reference die 31. FIG. 9B illustrates the images 45a to 45c that are portions of the image produced to represent the inspected die 33.

The thus sampled images (45a to 45c) corresponding to portions of the image of the inspected die 33 are compared with the alignment reference image 45. An image exhibiting the largest correlation value is selected from these sampled images. The position of the selected image within the domain 41c is compared with the position of the alignment reference image 45 within the domain 41a. Thus, a degree of pixel alignment to which the image of the reference die 31 that belongs to the image domain 41a and the image of the inspected die 33 that belongs to the image domain 41c are shifted to align with each other is calculated.

Thereafter, the image alignment unit 22 performs alignment by causing a shift to a degree measured in units of one pixel or less. This alignment shall be referred to as sub-pixel alignment. The sub-pixel alignment will be described below.

Herein, an image that is found to most highly correlate with the alignment reference image 45 during the pixel alignment shall be the image 45a.

The image alignment unit 22 produces an image 45a' by shifting the image 45a by a predetermined skip width (for example, to a degree measured in units of 0.1 pixel) ranging from −0.5 pixel to 0.5 pixel. This is shown in FIG. 10A to FIG. 10D.

Figure 10A:
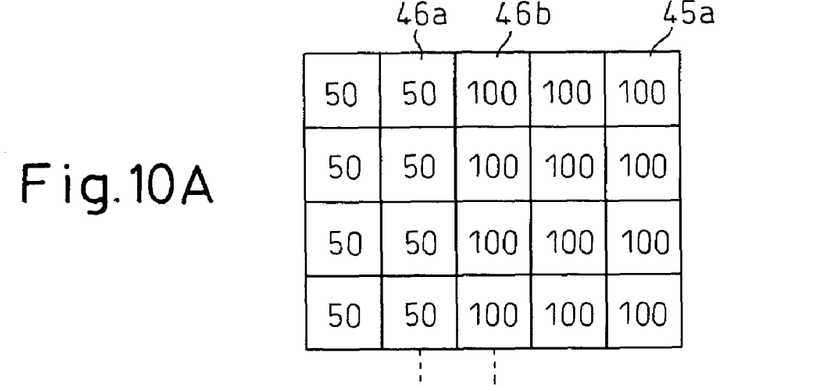
FIG. 10A to FIG. 10D are explanatory diagrams concerning sub-pixel alignment.
Figure 10B:
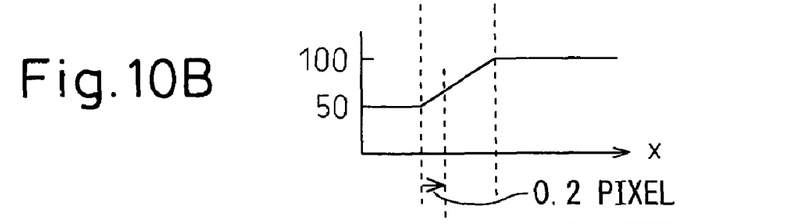

A description will be given of a procedure for producing an image by shifting the image 45a shown in FIG. 10A by 0.2 pixel in the x direction. Squares shown in FIG. 10A indicate pixels constituting the image 45a. Numerals written in the squares represent the gray-scale levels exhibited by the respective pixels.

Figure 10C:
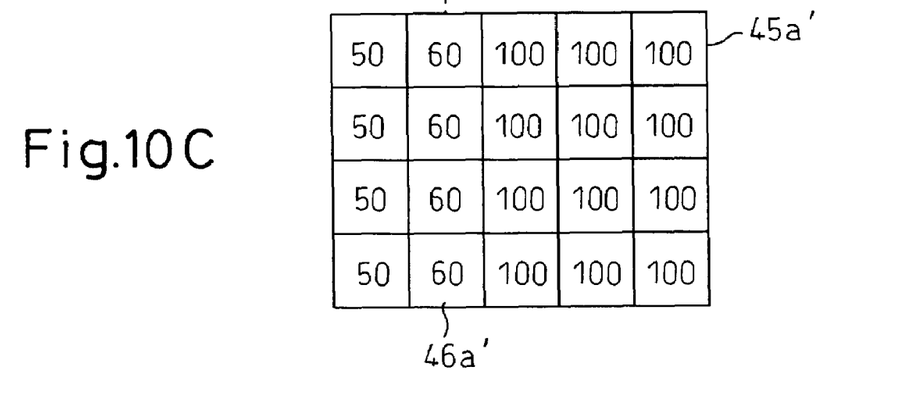
Figure 10D:
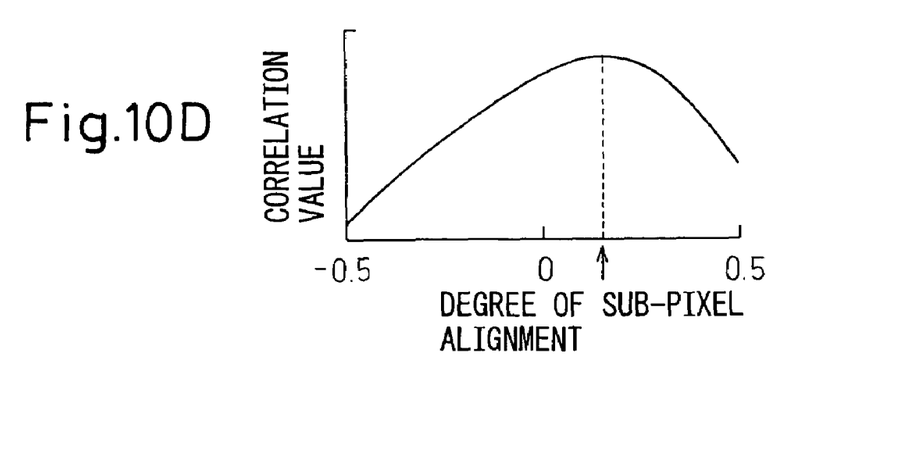

When the image 45a is shifted in the x direction, two pixel values adjoining in the x direction are generally used to interpolate the values of intermediate pixels by the number of which the position of one pixel is shifted. For example, referring to FIG. 10B, linear interpolation is adopted. Specifically, a linear function of a pixel value to a center position of a pixel is obtained from the spatial positions of the centers of the adjoining pixels 46a and 46b and their pixels values. Based on the linear function, a pixel value of which the pixel 46a assumes with the center position thereof shifted by 0.2 pixel is calculated. The pixel value shall be regarded as a pixel value of an associated pixel 46a' in an image produced by shifting the image 45a by 0.2 pixel. FIG. 10C shows the image 45a produced by shifting the image 45a shown in FIG. 10A by 0.2 pixel in the x direction.

A correlation value indicating the degree of correlation between each image 45a' produced by shifting the image 45a by a predetermined skip width and the alignment reference image 45 is calculated. Consequently, an approximate expression indicating the relationship between a degree of sub-pixel alignment and the correlation value is obtained (see FIG. 10D). A degree of sub-pixel alignment associated with the largest correlation value shall be adopted. Thus, a degree of sub-pixel alignment is calculated as a degree to which the image of the inspected die 33 belonging to the image domain 41c must be shifted to align with the image of the reference die 31 belonging to the image domain 41a.

The image alignment unit 22 performs the pixel alignment and sub-pixel alignment in both the x and y directions, and transmits calculated degrees of alignment to the difference detector 26. Based on the received information, the difference detector 26 samples an inspected frame contained in an image of an inspected pattern and an associated frame contained in an image of a reference pattern from the images stored in the image memory 20. Consequently, a difference-in-gray-scale level signal is produced relative to each of the pixels constituting the frames.

Based on the difference-in-gray-scale level signal produced by the difference detector 26, the defect verification unit 27 judges whether the difference-in-gray-scale level signal exceeds a predetermined threshold. If the signal exceeds the threshold, the signal is transmitted as a defective signal to the output unit 28.

By the way, as far as the foregoing conventional inspection machine is concerned, when a difference-in-gray-scale level signal is produced, a difference in a gray-scale level is corrected using information on adjoining pixels. This shall be referred to as edge factor handling. The edge factor handling is intended to minimize a possibility of incorrect detection of a defect. Specifically, an image of an edge of a pattern exhibits a greatly varying gray-scale level and suffers a larger noise than that of any other part thereof. The difference in a gray-scale level of the image of the pattern edge is therefore large. Consequently, the difference in a gray-scale level of the pattern edge image is detected as a smaller value.

For the edge factor handling, a differential filter is applied to pixels constituting either of an inspected frame and a reference frame in order to detect an image portion whose gray-scale level varies greatly, that is, a pattern edge image. The difference in a gray-scale level of the detected pattern edge image is reduced. A concrete procedure will be described below.

The differential filter shall be a 3×3 filter. A typical 3×3 filter is expressed as a formula (1) below where coefficients $a_{i,j}$ are predetermined constants.

$$A = \begin{pmatrix} a_{-1,-1} & a_{-1,0} & a_{-1,1} \\ a_{0,-1} & a_{0,0} & a_{0,1} \\ a_{-1,-1} & a_{1,0} & a_{1,1} \end{pmatrix} \quad (1)$$

Figure 11A:
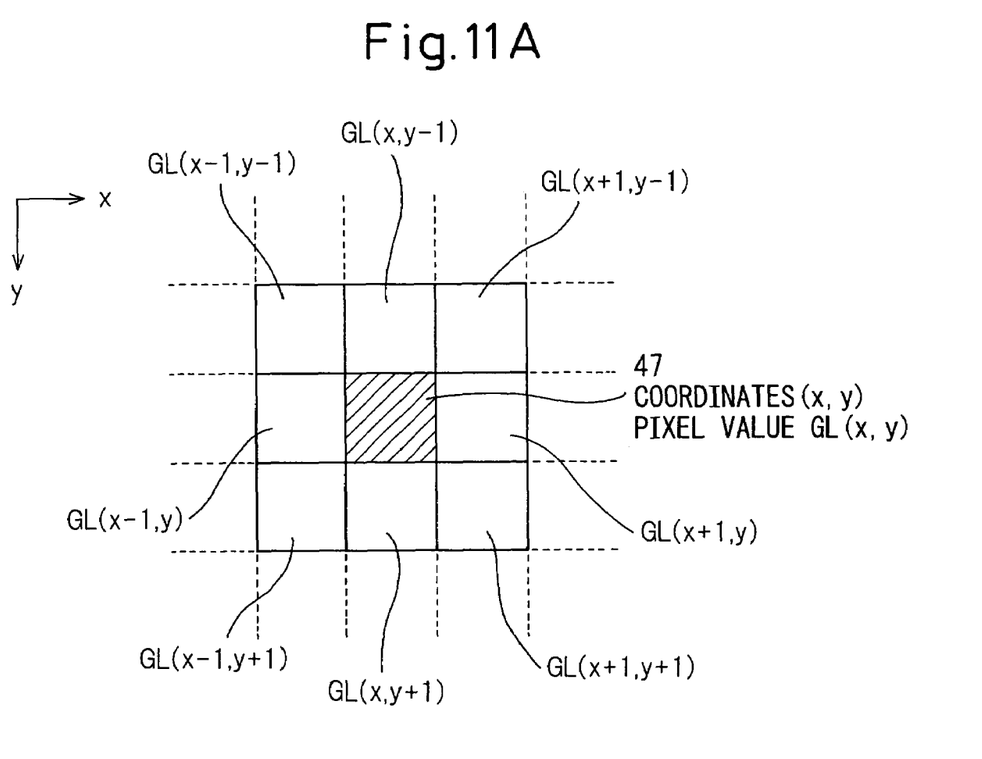
FIG. 11A to FIG. 11C are explanatory diagrams concerning typical 3×3 filtering.
Figure 11B:
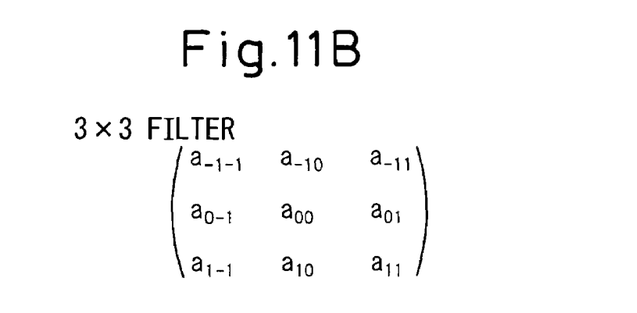
Figure 11C:
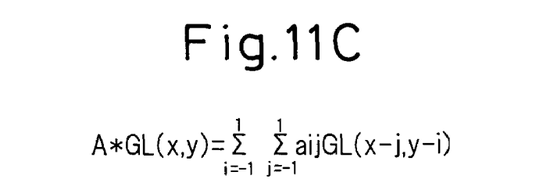

FIG. 11A shows a pixel 47 whose position is represented with coordinates (x, y) and surrounding pixels as well as their pixel values. As shown in FIG. 11A, the pixel value of a pixel at coordinates (x, y) shall be GL(x, y).

Assuming that the filter A is applied to the pixel 47, a pixel value A*GL(x, y) resulting from the filtering is calculated based on the own pixel value GL(x, y) and the surrounding pixel values according to a formula (2):

$$A * GL(x, y) = \sum_{i=-1}^{1} \sum_{j=-1}^{1} a_{i,j} GL(x+j, y+i) \quad (2)$$

Figure 12A:
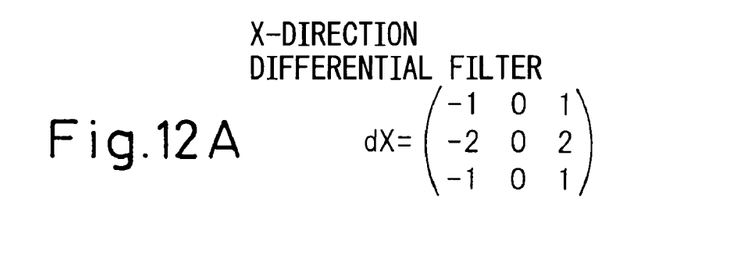
FIG. 12A to FIG. 12C are explanatory diagrams concerning edge factor handling in an x direction.
Figure 12B:
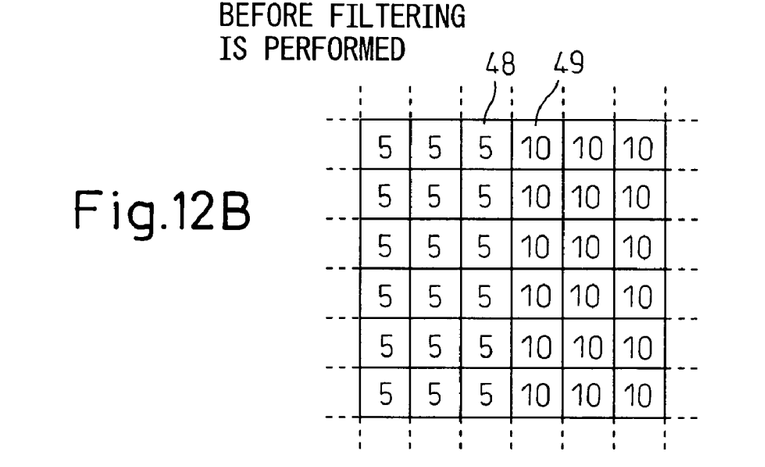

A differential filter dX for the x direction and a differential filter dY for the y direction are expressed as formulas (3) and (4) below. Assume that the x-direction differential filter expressed as the formula (3) is applied to each of pixels constituting an image shown in FIG. 12B. The image shown in FIG. 12B is an image in which pixel values vary in the x direction between a column starting with a pixel 48 and a column starting with a pixel 49, that is, within an edge pattern image.

$$dX = \begin{pmatrix} -1 & 0 & 1 \\ -2 & 0 & 2 \\ -1 & 0 & 1 \end{pmatrix} \quad (3)$$

$$dY = \begin{pmatrix} -1 & -2 & -1 \\ 0 & 0 & 0 \\ 1 & 2 & 1 \end{pmatrix} \quad (4)$$

Figure 12C:
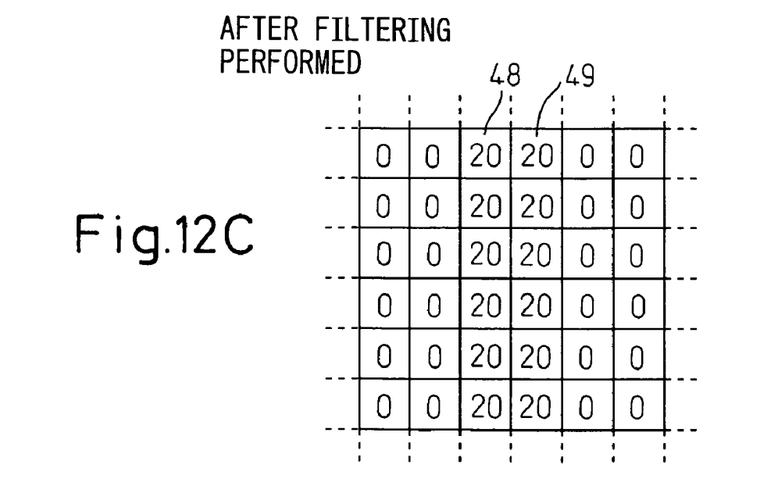

FIG. 12C shows an image that has undergone filtering. As shown in the drawing, pixel values are large only in the columns starting with the pixels 48 and 49, that is, in the edge pattern image. Consequently, the edge pattern image is detected. A difference in a gray-scale level ΔGL of each pixel is corrected according to a formula (5) below, whereby a difference in a gray-scale level of the edge image is minimized. In this case, a magnitude of correction is expressed as a formula (6).

corrected difference in a gray-scale level=ΔGL×(1−A
(|dX*GL(x, y)|+|dY*GL(x, y)|))   (5)

Magnitude of correction=ΔGL·A(|dX*GL(x, y)|+
|dY*GL(x, y)|)   (6)

Herein, GL(x, y) denotes a pixel value of a pixel at a position represented with coordinates (x, y), and A denotes a predetermined constant of proportion.

An edge factor handler 23 applies a differential filter 24 (including the x-direction and y-direction differential filters dX and dY) to each of pixels constituting an inspected image. Consequently, a variation in a gray-scale level of each pixel relative to that of other pixel adjoining in the x or y direction, that is, a differentiated value of each pixel value (differential-filtered value) is calculated. An image portion exhibiting a large differentiated value (change), that is, a pattern edge image is detected.

Moreover, a magnitude-of-correction determination unit 25 determines a magnitude of correction, by which a difference in a gray-scale level detected by the difference detector 26 is corrected, according to the formula (6) on the basis of a filtered image provided by the edge factor handler 23.

When dice are patterned, a condition for exposure or a condition for etching differs slightly from die to die. An edge of one die is therefore finished slightly differently from that of other die. An edge of a pattern formed on one die is therefore different from that of a pattern formed on other die. This is thought to be a main factor of the noise contained in an image of the pattern edge. The conventional edge factor handling for reducing a difference in a gray-scale level of a pattern edge image is based on this idea.

However, a pattern edge image suffers not only the above noise attributable to an error of the pattern edge but also a noise attributable to the sub-pixel alignment. This is because whatever interpolation is employed in the sub-pixel alignment, a gray-scale level of a pattern edge image resulting from the sub-pixel alignment differs from that of an actually produced image of a pattern edge.

An error occurring in correction of the sub-pixel alignment depends on a degree of sub-pixel alignment. However, conventionally, a difference in a gray-scale level is uniformly corrected (through edge factor handling) according to the formula (5).

Therefore, conventionally, the edge factor handler 23 is designed so that it will not detect a defect despite the largest possible noise that is predicted in consideration of an error in correction of the sub-pixel alignment. This degrades the sensitivity in detecting a defective pattern edge image.

SUMMARY OF THE INVENTION

Accordingly, an object of the present invention is to improve the sensitivity in detecting a defective pattern edge image by modifying a procedure for determining a magnitude of correction by which a difference in a gray-scale level of a pattern edge image is corrected (edge factor handling).

In order to accomplish the above object, according to the first aspect of the present invention, there is provided a defect inspecting method that determines a magnitude of correction, by which a difference in a gray-scale level of a pattern edge image between images is corrected, on the basis of a detected degree of sub-pixel alignment (that is, a sub-pixel deviation between two images, between which a difference in a gray-scale level of each pixel is calculated, from the other image).

As mentioned above, a magnitude of correction by which a difference in a gray-scale level of a pattern edge image is corrected is determined based on the degree of sub-pixel alignment. Consequently, a reduction in the difference in a gray-scale level of the pattern edge image can be increased or decreased based on the error in correction of sub-pixel alignment which is produced by a noise occurring in the pattern edge image. Consequently, the sensitivity in detecting a defective pattern edge image can be improved.

Figure 1:
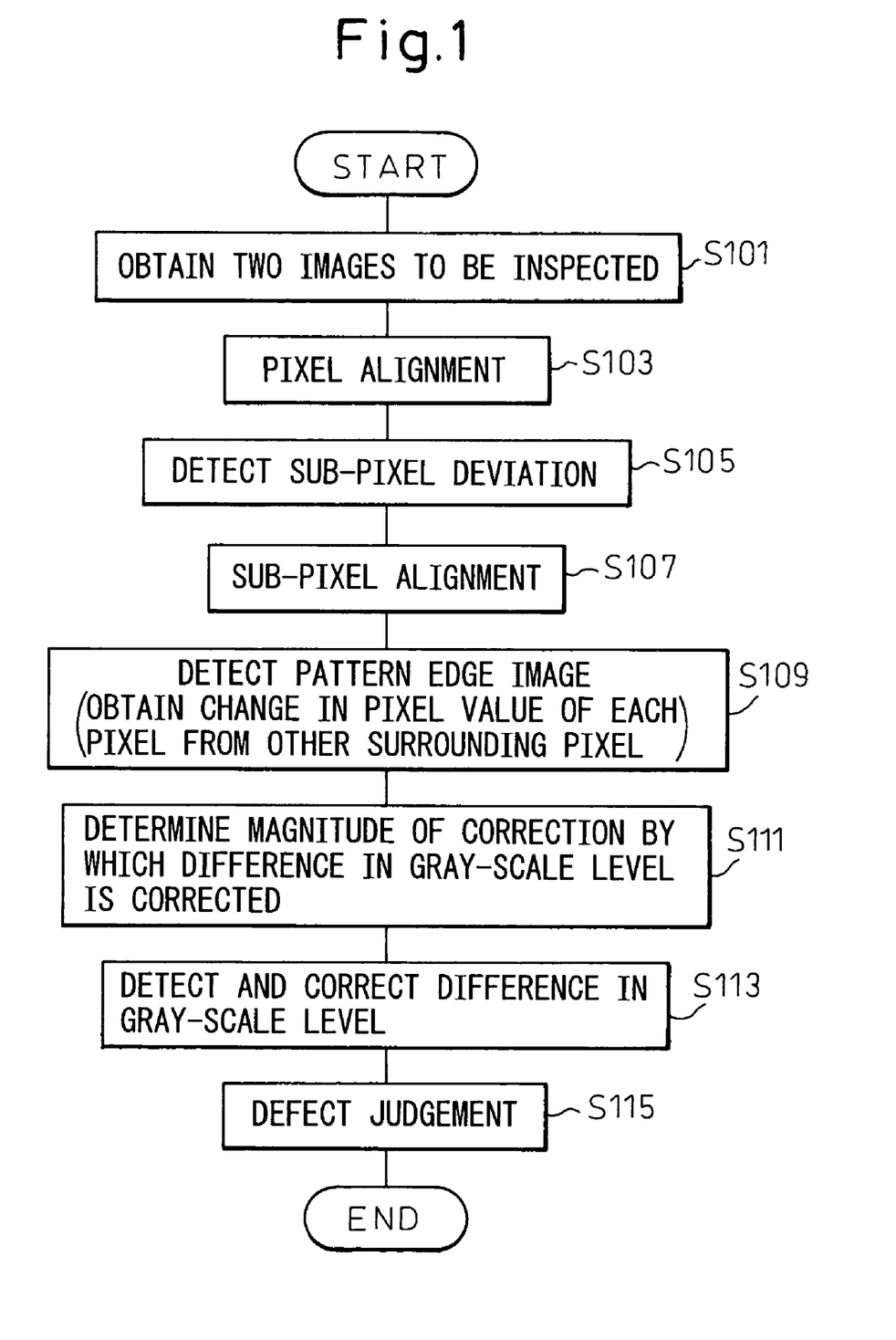
FIG. 1 is a flowchart (part 1) describing a defect inspecting method in accordance with the present invention.

FIG. 1 is a flowchart describing a defect inspecting method in accordance with the first aspect of the present invention.

At step S101, two images derived from two objects to be inspected are obtained.

At step S103, if said two images are deviated from each other to a degree measured in units of a pixel, pixel alignment is performed. Specifically, pixels constituting said two images that are compared with each other in order to detect a difference in a gray-scale level are shifted to a degree measured in units of a pixel.

At step S105, a deviation of said two images from each other which is smaller than one pixel (a sub-pixel deviation or a degree of sub-pixel alignment) is detected.

At step S107, if said images are deviated from each other to a degree smaller than one pixel, sub-pixel alignment is performed. Specifically, one of said two images or both thereof are shifted by the sub-pixel deviation (degree of sub-pixel alignment) from the other image or from the other images.

At step S109, a pattern edge image is detected from one or both of said two images.

At step S111, a magnitude of correction by which a difference in a gray-scale level of each pixel is corrected is determined based on the sub-pixel deviation detected at step S105 and the information on the pattern edge image that is detected at step S109.

At step S113, a difference in a gray-scale level of each pixel between said two images that are objects of inspection is detected. At this time, the difference in a gray-scale level is corrected by the magnitude of correction determined at step S111.

At step S115, the difference in a gray-scale level detected at step S113 is compared with a predetermined threshold. It is judged whether one of said two objects is defective.

A defect inspecting apparatus in accordance with the second aspect of the present invention comprises: an image alignment unit that detects a sub-pixel deviation (degree of sub-pixel alignment) between two images between which a difference in a gray-scale level is detected; and a magnitude-of-correction determination unit that determines a magnitude of correction by which a difference in a gray-scale level of a pattern edge image between these images, which is detected by the difference detector, is corrected.

Furthermore, an inspection machine in accordance with the third aspect of the present invention comprises the defect inspecting apparatus according to the second aspect of the present invention that compares substantially the same patterns, which are formed on a semiconductor wafer, with each other so as to detect a defective semiconductor circuit pattern.

DESCRIPTION OF THE PREFERRED EMBODIMENTS

Figure 2:
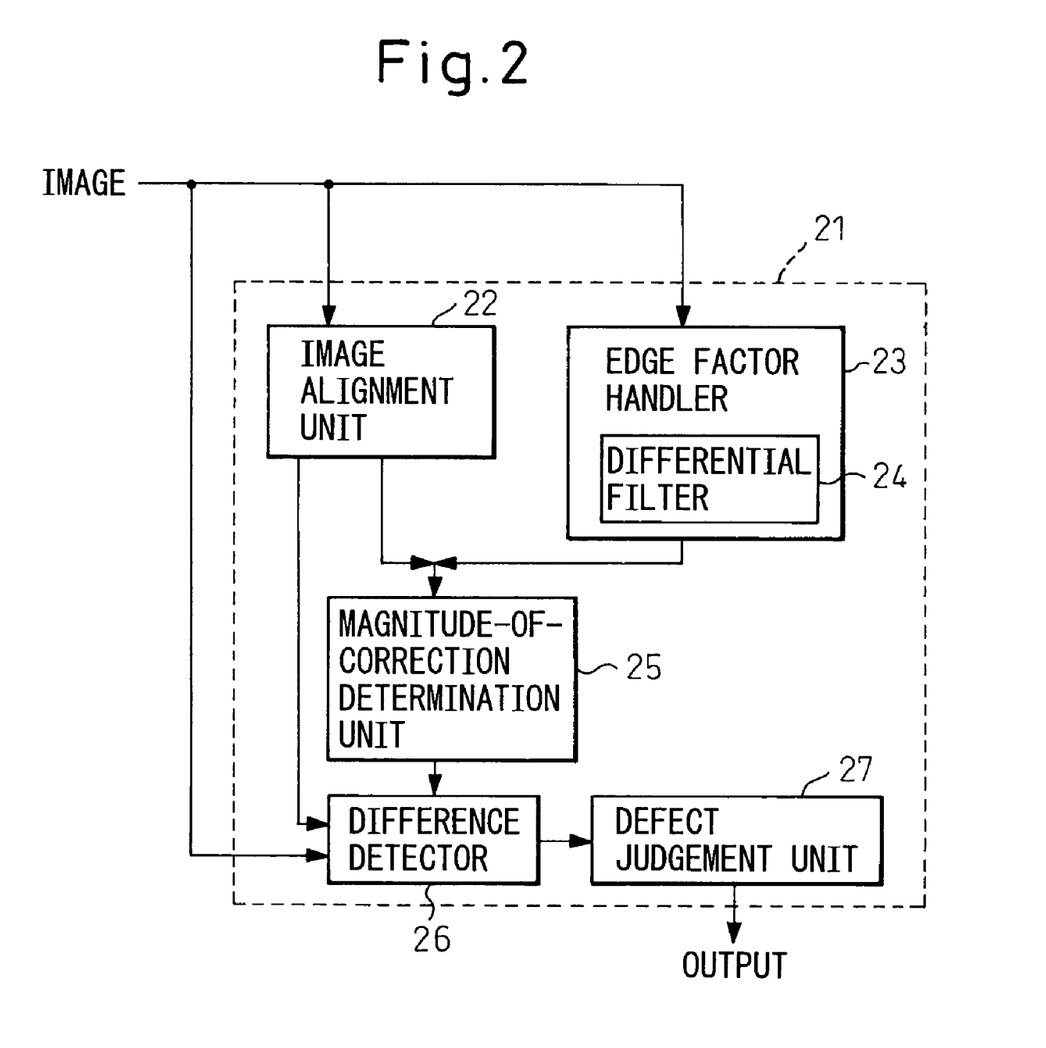
FIG. 2 schematically shows the configuration of a defect inspecting system in accordance with a first embodiment of the present invention.

Referring to the appended drawings, embodiments of the present invention will be described below. FIG. 2 schematically shows the configuration of a defect inspecting apparatus in accordance with a first embodiment of the present invention. A defect inspecting system 21 detects a difference in a gray-scale level of each pixel between two images representing substantially the same patterns. If the detected difference in a gray-scale level exceeds a predetermined threshold, it is judged that one of the two patterns is defective. Thus, the patterns are inspected to see if there is a defective pattern.

The defect inspecting apparatus 21 receives an inspected image and a reference image. The inspected image and reference image contain images that represent substantially the same patterns which must be inspected to see if the patterns are identical to others. The defect inspecting apparatus 21 comprises: an image alignment unit 22 that detects a degree of pixel alignment and a degree of sub-pixel alignment to which the two input images must be shifted to align with each other, and that aligns the images with each other; a difference detector 26 that detects a difference in a gray-scale level of each pixel between the two images; and a detect judgment unit 27 that compares the detected difference in a gray-scale level with a predetermined threshold and that, if the detected difference in a gray-scale level exceeds the threshold, judges that the pattern in the inspected image is defective.

Moreover, the defect inspecting apparatus 21 comprises: an edge factor handler 23 that detects a change (that is, a differentiated value or a differential-filtered value) in a pixel value in at least one of two images, and detects a pattern edge image; and a magnitude-of-gray-scale level correction determination unit 25 that, when the difference detector 26 detects a difference in a gray-scale level, determines a magnitude of correction, by which the difference in a gray-scale level is corrected, on the basis of the detected change in a pixel value and the degree of sub-pixel alignment.

Figure 3:
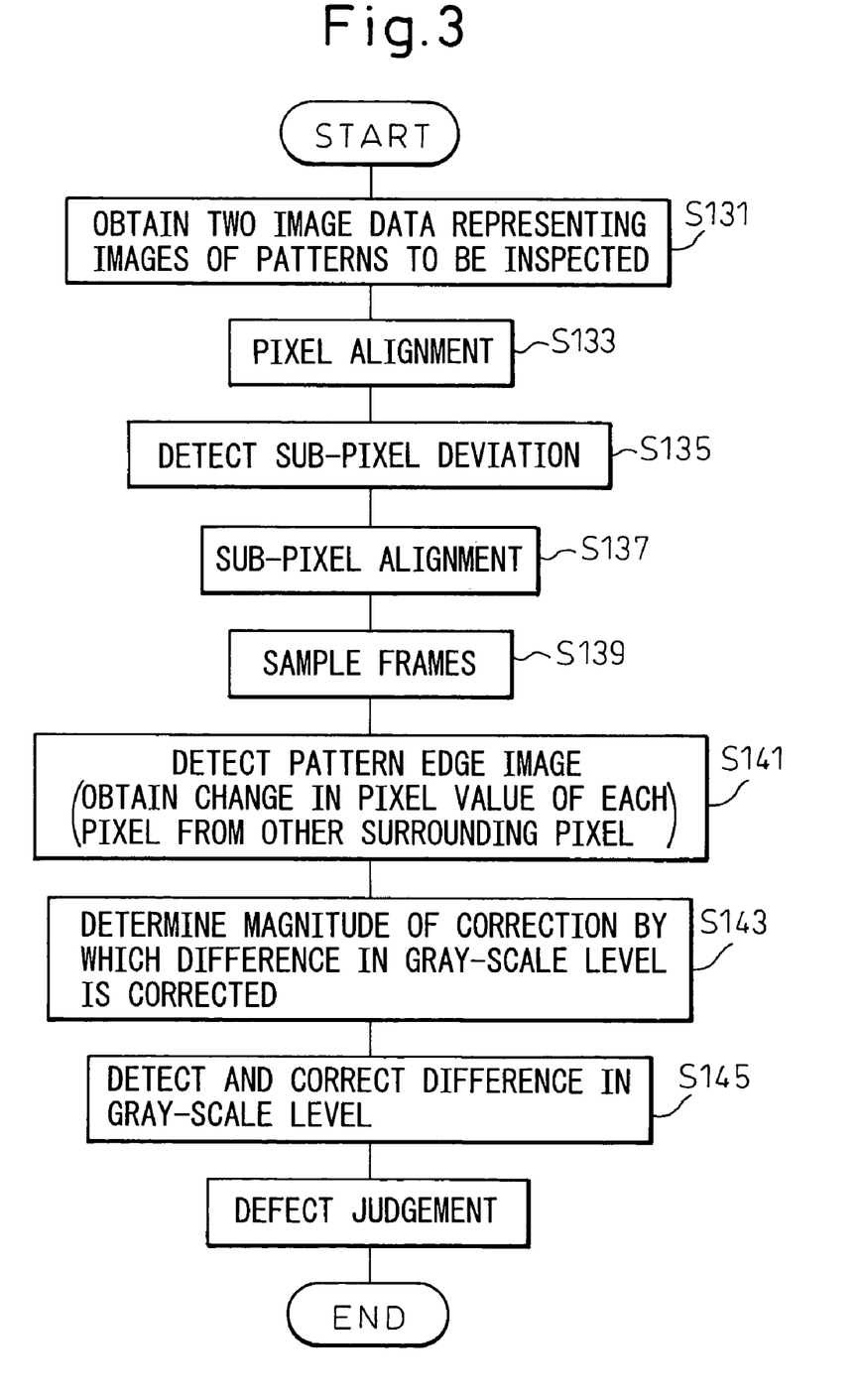
FIG. 3 is a flowchart (part 2) describing the defect inspecting method in accordance with the present invention.

Referring to the flowchart of FIG. 3 describing a defect inspecting method in accordance with the present invention, actions to be performed in the defect inspecting apparatus 21 will be described below.

First, at step S131, two image data representing images of patterns that are objects of defect inspection are transferred to the image alignment unit 22 and edge factor handler 23. For example, two image data representing images of patterns that are objects of inspection are sampled from among image data stored in an image memory or an external storage device.

At step S133, if the positions of the pattern images represented by the two image data items are deviated from each other to a degree measured in units of a pixel, the alignment unit 22 performs the foregoing pixel alignment.

At step S135, the image alignment unit 22 detects a degree of sub-pixel alignment to which the pattern images represented by the two image data items must be shifted to align with the other. A detected degree of sub-pixel alignment in the x direction shall be $Shift_x$, and a detected degree of sub-pixel alignment in the y direction shall be $Shift_y$.

At step S137, if the pattern images are deviated from each other to a degree corresponding to a pixel or less, the image alignment unit 22 performs sub-pixel alignment.

At step S139, a block of pixels (frame) is sampled from each of the two image data representing the pattern images whose positions are adjusted through the pixel alignment and sub-pixel alignment.

In reality, detection of a degree of sub-pixel alignment alone may be performed during sub-pixel alignment (S135). The positions of the pattern images represented by the image data may be adjusted during pixel alignment alone (S133). Adjusting the positions of the pattern images during sub-pixel alignment at step S137 may be omitted.

According to the conventional defect inspecting method, if adjusting the positions of the pattern images during sub-pixel alignment is omitted, a quasi defect is likely to be detected because of an increase in a difference in a gray-scale level of a pattern edge image. In contrast, according to the defect inspecting method of the present invention, as described later (S143 and S145), if a degree of alignment is large, the sensitivity in detecting a difference in a gray-scale level of a pattern edge image is lowered. Therefore, detection of a quasi defect deriving from a sub-pixel deviation can be prevented.

At step 141, a pattern edge image is detected in one or both of the frames contained in the image data. For example, the x-direction differential filter dX and y-direction differential filter dY expressed as the formulas (2) and (3) are applied to each pixel of image data. A differentiated value (differential-filtered value) of each pixel value, that is, a change in a gray-scale level of each pixel from other surrounding pixels in the x direction, and a change in the gray-scale level of each pixel from other surrounding pixels in the y direction are detected. An image represented by pixels exhibiting large changes in a gray-scale level is detected as a pattern edge image.

At step S143, the magnitude-of-correction determination unit 25 determines a magnitude of correction, by which a difference in a gray-scale level of each pixel is corrected, on the basis of the degree of sub-pixel alignment detected at step S135. The action of the magnitude-of-correction determination unit will be described with reference to FIG. 4. FIG. 11A shows a pixel 47 whose position is represented with coordinates (x, y) and surrounding pixels as well as respective pixel values. As shown in the drawing, a pixel whose position is represented with coordinates (x, y) shall assume a pixel value GL(x, y).

Figure 4:
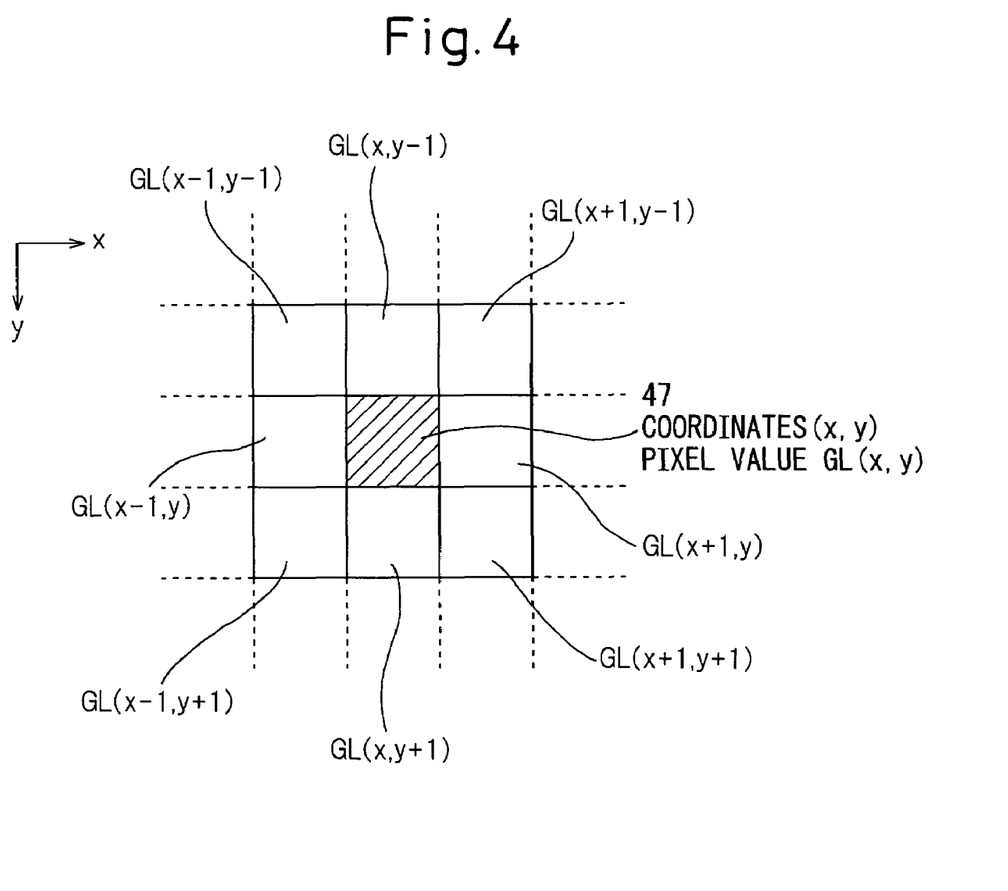
FIG. 4 is an explanatory diagram concerning a procedure for determining a magnitude of correction by which a difference in a gray-scale level is corrected.

Assuming that the x-direction differential filter dX is applied to a pixel at coordinates (x, y), the pixel value resulting from the filtering shall be dX*GL(x, y). Assuming that the y-direction differential filter dY is applied to a pixel at coordinates (x, y), the pixel value resulting from the filtering shall be dY*GL(x, y). In this case, a magnitude of correction M by which a difference in a gray-scale level of each pixel (x, y) corrected is determined according to a formula (7) below.

$$M = \Delta GL \cdot g(Shift_x, Shift_y) \cdot (|dX^*GL(x, y)| + |dY^*GL(x, y)|) \quad (7)$$

The function g can be defined according to the kind of image data employed. For example, the function g may be defined as a formula (8):

$$g(Shift_x, Shift_y) = -a(|Shift_x| + |Shift_y|) + b \quad (8)$$

where a and b denote constants. Preferably, the function g is a decreasing function of the degrees of sub-pixel alignment $|Shift_x|$ and $|Shift_y|$.

At step S145, the difference detector 26 detects a difference in a gray-scale level of each pixel between two frames of the two image data representing the pattern images that are inspected. At this time, based on the magnitude of correction determined at step S143, the difference detector 26 corrects the difference in a gray-scale level. The difference in a gray-scale level of each pixel, $\Delta GL'$, is defined as a formula (9) below.

$$\Delta GL' = \Delta GL \cdot \{1 + g(Shift_x, Shift_y) \cdot (|dX^*GL(x, y)| + |dY^*GL(x,y)|)\} \quad (9)$$

where $\Delta GL$ denotes a difference in a gray-scale level, and $\Delta GL'$ denotes a corrected difference in a gray-scale level.

Alternatively, the degrees of sub-pixel alignment $Shift_x$ and $Shift_y$ and the pixel values dX*GL(x, y) and dY*GL(x, y) resulting from filtering may be directly transferred to the difference detector 26. A difference in a gray-scale level may then be calculated according to a formula (10).

$$\Delta GL' = f(\Delta GL, dX^*GL(x,y), dY^*GL(x,y), Shift_x, Shift_y) \quad (10)$$

Preferably, the function f is a decreasing function of the degrees of sub-pixel alignment $|Shift_x|$ and $|Shift_y|$.

At step S147, the defect verification unit 27 compares the difference in a gray-scale level detected at step S145 with the predetermined threshold, and judges that the pattern whose image is represented by one of the frames and that is an object of inspection is defective.

As mentioned above, the defect inspecting apparatus 21 in accordance with the present invention can increase or decrease a magnitude of correction, by which a difference in a gray-scale level of a pattern edge image is corrected, according to a degree of sub-pixel alignment to which images that are objects of inspection are shifted to align with each other. In other words, the sensitivity in detecting a defective pattern edge image can be varied depending on an error in correction of sub-pixel alignment. For example, when a large error is predicted to occur in correction of sub-pixel alignment, the magnitude of correction by which a difference in a gray-scale level is corrected is increased in order to lower the sensitivity in detecting a defective pattern edge image. In contrast, when a small error is predicted to occur in correction of sub-pixel alignment, the magnitude of correction by which the difference in a gray-scale level is corrected is decreased in order to raise the sensitivity in detecting a defective pattern edge image. Consequently, the sensitivity in detecting a defective pattern edge image can be improved, though the sensitivity has been set to a level lower than a required level in the conventional defect inspecting system.

Figure 5:
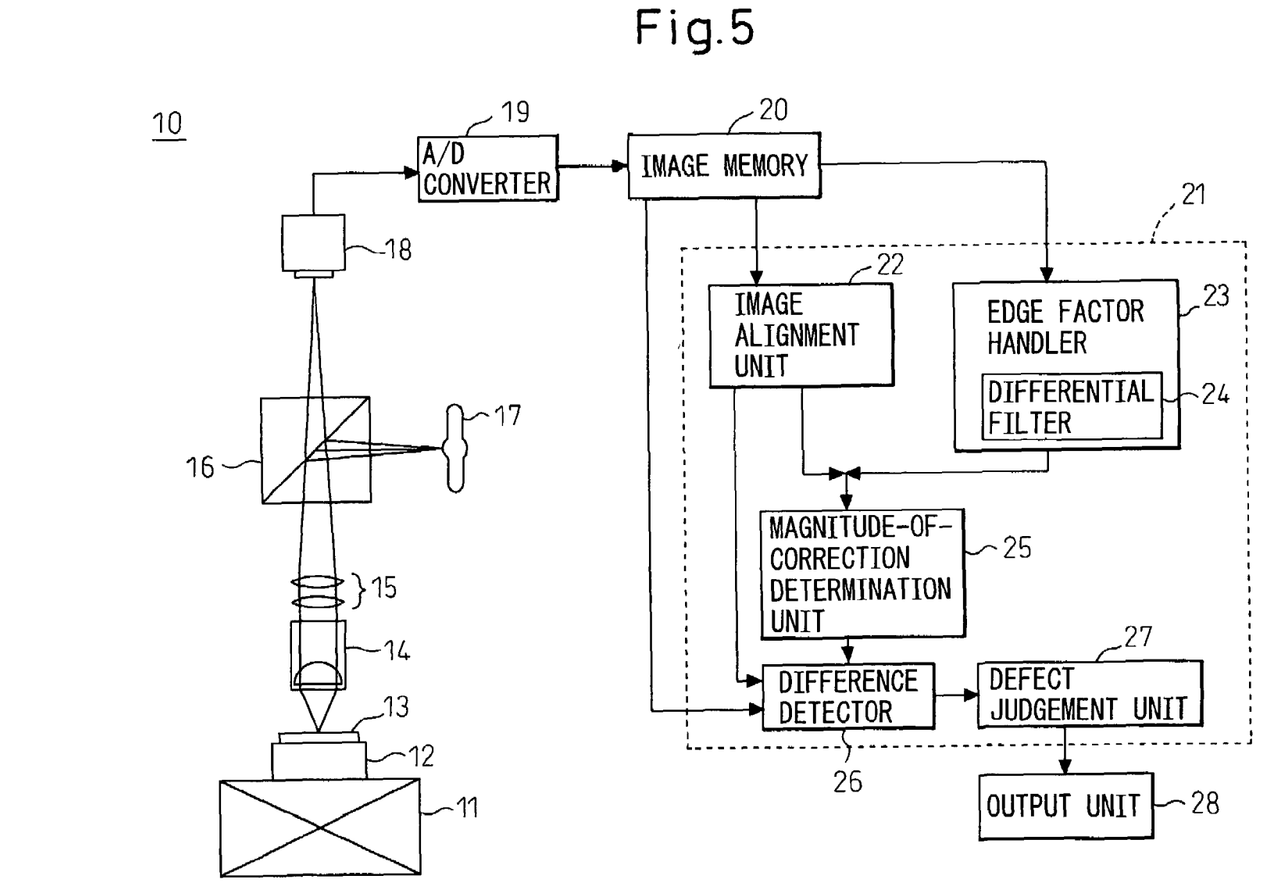
FIG. 5 schematically shows the configuration of a defect inspecting system in accordance with a second embodiment of the present invention.

FIG. 5 schematically shows the configuration of a semiconductor device inspection machine in accordance with a second embodiment of the present invention. The configuration of the inspection machine in accordance with the present embodiment is analogous to the configuration shown in FIG. 6. The same reference numerals will be assigned to identical facilities, and a description of the facilities will be omitted.

An inspection machine 10 of the present embodiment comprises the defect inspecting apparatus 21 in accordance with the first embodiment of the present invention.

When the xy stage 11 moves the wafer 13, the imaging unit 18 scans the wafer 13 in the x and y directions and images the entire surface of the wafer 13. A signal produced by the imaging unit 18 is stored in the image memory 20 after analog-to-digital converted.

The image alignment unit 22 included in the defect inspecting apparatus 21 samples an image domain 41c, which includes an inspected frame which represents an inspected die 33, and an image domain 41a, which includes a reference frame which represents a reference die 31, located at a position corresponding to the position of the inspected domain 41c (see FIG. 8A), from the image memory 20. The image alignment unit 22 then detects a degree of pixel alignment and a degree of sub-pixel alignment to which the images represented by the image domains 41a and 41c are shifted to align with each other. The inspected frame and reference frame are sampled from the image domains 41c and 41a that have undergone alignment and represent the inspected die 33 and reference die 31 respectively.

The edge factor handler 23 included in the defect inspecting apparatus 21 detects a change in a pixel value of each pixel, which is contained in at least one of two frames, from other surrounding pixel, and thus detects a pattern edge image. This is achieved by applying the differential filter 24 to each pixel contained in at least one of the two frames.

The magnitude-of-gray-scale level correction determination unit 25 determines a magnitude of correction, by which a difference in a gray-scale level is corrected, on the basis of the detected change in a pixel value and the degree of sub-pixel alignment. Therefore, the difference in a gray-scale level of a pattern edge image can be corrected, when the difference detector 26 detects a difference in a gray-scale level.

Based on the determined magnitude of correction, the difference detector 26 detects a difference in a gray-scale level of each pixel between the two frames. The defect verification unit 27 compares the detected difference in a gray-scale level with a predetermined threshold. If the difference in a gray-scale level exceeds the threshold, the defect verification unit 27 judges that the inspected die is defective.

When an inspection machine is designed as in the present embodiment, the sensitivity in detecting a defective pattern edge image representing an edge of a semiconductor circuit pattern formed on a semiconductor wafer can be improved.

According to an image defect inspecting method of the present invention, a reduction in a difference in a gray-scale level of a pattern edge image can be increased or decreased based on an error in correction of sub-pixel alignment that is produced by a noise affecting the pattern edge image. The sensitivity in detecting a defective pattern edge image can be improved.

While the invention has been described with reference to specific embodiments chosen for purposes of illustration, it should be apparent that numerous modifications could be made thereto, by those skilled in the art, without departing from the basic concept and scope of the invention.

What is claimed is:

1. A defect inspecting method comprising the steps of:
   detecting a difference in a gray-scale level between corresponding portions of two images derived from two objects;
   comparing the detected difference in a gray-scale level with a predetermined threshold;
   if the difference in a gray-scale level is larger than the threshold, judging that one of the objects is defective;
   detecting a sub-pixel deviation of the two images from each other; and
   determining a magnitude of correction, by which the difference in a gray-scale level of a pattern edge image between the images is corrected, according to the detected sub-pixel deviation.

2. A defect inspecting method according to claim 1, wherein the magnitude of correction is determined so that the difference in a gray-scale level of the pattern edge image between the images decreases with an increase in the sub-pixel deviation.

3. A defect inspecting method according to claim 1, wherein determining a magnitude of correction comprises applying a differential filter to each of the pixels constituting at least one of the two images to calculate a differential-filtered value, wherein the magnitude of correction by which the difference in a gray-scale level of each pixel is corrected is determined based on a function of the differential-filtered value of each pixel value relative to the sub-pixel deviation.

4. A defect inspecting method according to claim 3, wherein the magnitude of correction is determined based on a product of the differential-filtered value of each pixel value by a function of the sub-pixel deviation.

5. A defect inspecting apparatus comprising:
   a difference detector that detects a difference in a gray-scale level between corresponding portions of two images derived from two objects;
   a defect judgement unit that compares the detected difference in a gray-scale level with a predetermined threshold, and that if the difference in a gray-scale level is larger than the threshold, judges that one of the objects is defective;
   an image alignment unit that detects a sub-pixel deviation of the two images from each other; and
   a magnitude-of-correction determination unit that determines a magnitude of correction, by which the difference in a gray-scale level of a pattern edge image between the images that is detected by said difference detector is corrected, according to the detected sub-pixel deviation.

6. A defect inspecting apparatus according to claim 5, wherein said magnitude-of-correction determination unit determines the magnitude of correction so that the difference in a gray-scale level of a pattern edge image between the images decreases with an increase in the sub-pixel deviation.

7. An inspection machine including the defect inspecting apparatus in accordance with claim 6, for detecting a defective semiconductor circuit pattern formed on a semiconductor wafer, said inspection machine comprising:
   an imaging unit that produces images of the semiconductor circuit patterns formed on said semiconductor wafer, wherein:
   said defect inspecting apparatus compares substantially identical patterns, which are formed on said semiconductor wafer, with each other so as to detect a defective semiconductor circuit pattern.

8. A defect inspecting apparatus according to claim 5, further comprising a differential filter used to calculate a differentiated value of a value of each pixel contained in the images, wherein:

said magnitude-of-correction determination unit determines a magnitude of correction, by which the difference in a gray-scale level of each pixel is corrected, according to a function of the differential-filtered value of a value of each pixel contained in at least one of the two images, which is calculated using said differential filter, relative to the sub-pixel deviation.

9. A defect inspecting apparatus according to claim 8, wherein said magnitude-of-correction determination unit determines the magnitude of correction according to a product of the differential-filtered value of each pixel value by a function of the sub-pixel deviation.

10. An inspection machine including the defect inspecting apparatus in accordance with claim 9, for detecting a defective semiconductor circuit pattern formed on a semiconductor wafer, said inspection machine comprising:

an imaging unit that produces images of the semiconductor circuit patterns formed on said semiconductor wafer, wherein:

said defect inspecting apparatus compares substantially identical patterns, which are formed on said semiconductor wafer, with each other so as to detect a defective semiconductor circuit pattern.

11. An inspection machine including the defect inspecting apparatus in accordance with claim 8, for detecting a defective semiconductor circuit pattern formed on a semiconductor wafer, said inspection machine comprising:

an imaging unit that produces images of the semiconductor circuit patterns formed on said semiconductor wafer, wherein:

said defect inspecting apparatus compares substantially identical patterns, which are formed on said semiconductor wafer, with each other so as to detect a defective semiconductor circuit pattern.

12. An inspection machine including the defect inspecting apparatus in accordance with claim 5, for detecting a defective semiconductor circuit pattern formed on a semiconductor wafer, said inspection machine comprising:

an imaging unit that produces images of the semiconductor circuit patterns formed on said semiconductor wafer, wherein:

said defect inspecting apparatus compares substantially identical patterns, which are formed on said semiconductor wafer, with each other so as to detect a defective semiconductor circuit pattern.

* * * * *